(12) United States Patent
Mulye

(10) Patent No.: US 8,545,882 B2
(45) Date of Patent: *Oct. 1, 2013

(54) CONTROL RELEASE FORMULATION CONTAINING A HYDROPHOBIC MATERIAL AS THE SUSTAINED RELEASE AGENT

(75) Inventor: Nirmal Mulye, Princeton, NJ (US)

(73) Assignee: Nostrum Pharmaceuticals, Inc., Princeton, NJ (US)

( * ) Notice: Subject to any disclaimer, the term of this patent is extended or adjusted under 35 U.S.C. 154(b) by 1145 days.

This patent is subject to a terminal disclaimer.

(21) Appl. No.: 11/355,346

(22) Filed: Feb. 16, 2006

(65) Prior Publication Data

US 2006/0204573 A1    Sep. 14, 2006

Related U.S. Application Data

(63) Continuation of application No. 10/167,368, filed on Jun. 10, 2002, now Pat. No. 7,052,706.

(60) Provisional application No. 60/297,140, filed on Jun. 8, 2001.

(51) Int. Cl.
*A61K 9/20* (2006.01)
*A61K 9/28* (2006.01)

(52) U.S. Cl.
USPC .......................................... 424/464; 424/474

(58) Field of Classification Search
None
See application file for complete search history.

(56) References Cited

U.S. PATENT DOCUMENTS

| | | |
|---|---|---|
| 3,965,256 A | 6/1976 | Leslie |
| 4,132,753 A | 1/1979 | Blichare et al. |
| 4,138,475 A | 2/1979 | McAinsh et al. |
| 4,199,585 A | 4/1980 | Vegezzi |
| 4,235,870 A | 11/1980 | Leslie |
| 4,248,857 A | 2/1981 | DeNeale et al. |
| 4,252,786 A | 2/1981 | Weiss et al. |
| 4,375,468 A | 3/1983 | Dunn |
| 4,389,393 A * | 6/1983 | Schor et al. .................... 424/469 |
| 4,443,428 A | 4/1984 | Oshlack et al. |
| 4,587,118 A | 5/1986 | Hsiao |
| 4,590,062 A | 5/1986 | Jang |
| 4,610,870 A | 9/1986 | Jain et al. |
| 4,634,587 A | 1/1987 | Hsiao |
| 4,692,337 A | 9/1987 | Ukigaya et al. |
| 4,713,626 A | 12/1987 | Susak et al. |
| 4,752,470 A | 6/1988 | Mehta |
| 4,756,911 A | 7/1988 | Drost et al. |
| 4,789,549 A | 12/1988 | Khan et al. |
| 4,800,084 A | 1/1989 | Zerbe |
| 4,834,985 A | 5/1989 | Elger et al. |
| 4,882,167 A | 11/1989 | Jang |
| 4,898,737 A | 2/1990 | Panoz et al. |
| 5,023,089 A | 6/1991 | Sakamoto et al. |
| 5,091,189 A | 2/1992 | Heafield et al. |
| 5,126,145 A | 6/1992 | Evenstad et al. |
| 5,169,645 A | 12/1992 | Shukla et al. |
| 5,213,811 A | 5/1993 | Frisbee et al. |
| 5,268,181 A | 12/1993 | O'Neill et al. |
| 5,273,760 A | 12/1993 | Oshlack et al. |
| 5,376,384 A | 12/1994 | Eichel et al. |
| 5,456,920 A | 10/1995 | Matoba et al. |
| 5,464,633 A | 11/1995 | Conte et al. |
| 5,472,712 A | 12/1995 | Oshlack et al. |
| 5,478,573 A | 12/1995 | Eichel et al. |
| 5,500,227 A | 3/1996 | Oshlack et al. |
| 5,591,452 A | 1/1997 | Miller et al. |
| 5,650,169 A | 7/1997 | Conte et al. |
| 5,651,984 A | 7/1997 | Powell |
| 5,681,585 A | 10/1997 | Oshlack et al. |
| 5,690,959 A * | 11/1997 | Palepu et al. .................. 424/472 |
| 5,700,410 A | 12/1997 | Nakamichi et al. |
| 5,824,344 A | 10/1998 | Palepu et al. |
| 5,843,480 A | 12/1998 | Miller et al. |
| 5,849,240 A | 12/1998 | Miller et al. |

(Continued)

FOREIGN PATENT DOCUMENTS

| | | |
|---|---|---|
| WO | WO 97/32584 | 9/1997 |
| WO | WO 00/01416 | 1/2000 |

OTHER PUBLICATIONS

Clarithromycin. The Merck Index. Accessed online on Apr. 10, 2009 at www.knovel.com.*
"Clarithromycin". The Merck Index. Accessed online on Apr. 10, 2009 at www.knovel.com.*
Dakkuri A. et al. "Sustained Release from Inert Wax Matrixes III: Effect of Povidone on Tripelennamine Hydrochloride Release" 1978, 357-340, vol. 67, No. 3, Journal of Pharmaceutical Sciences.

(Continued)

*Primary Examiner* — Carlos Azpuru
*Assistant Examiner* — Casey Hagopian
(74) *Attorney, Agent, or Firm* — Scully, Scott, Murphy & Presser, P.C.

(57) ABSTRACT

The present invention is directed to a sustained release pharmaceutical composition in oral dosage form consisting essentially of a pharmaceutically effective amount of a medicament and a hydrophobic material in the absence of a lactose or hydrophobic carbohydrate polymer, said medicament being present in an amount greater than about 25% of the pharmaceutical composition and having a water solubility greater than about 1 gram per 10 mL of water at 25° C., said hydrophobic material having a melting point ranging from at least about 40° C. to about 100° C. at 1 atm pressure, and being present in an amount ranging from about 3% to about 20% by weight of the pharmaceutical composition and in an amount less than the of the medicament, and said hydrophobic material not being present in coating of said pharmaceutical composition; said pharmaceutical composition being prepared by direct compression in the absence of or melting the hydrophobic material or the use of high shear mixer. The present invention is also directed to a method of preparing said pharmaceutical composition.

26 Claims, No Drawings

(56) References Cited

U.S. PATENT DOCUMENTS

| | | | |
|---|---|---|---|
| 5,879,705 | A | 3/1999 | Heafield et al. |
| 5,891,471 | A | 4/1999 | Miller et al. |
| 5,958,459 | A | 9/1999 | Chasin et al. |
| 5,965,163 | A | 10/1999 | Miller et al. |
| 6,033,685 | A | 3/2000 | Qiu et al. |
| 6,039,974 | A | 3/2000 | MacLaren et al. |
| 6,379,700 | B2 | 4/2002 | Joachim et al. |
| 7,052,706 | B2* | 5/2006 | Mulye .................... 424/401 |
| 2002/0044968 | A1* | 4/2002 | van Lengerich ......... 424/469 |
| 2002/0182275 | A1 | 12/2002 | He et al. |

OTHER PUBLICATIONS

Abramocivi, et al., "Comparative Study on the Lubricating Properties of a New Additive: The Glycerol Tribehenate* (COMPRITOL 888) Compared to Magnesium Stearate", *Bulletin Technique Gattefosse* 78: 75-85 (1985).

Lipps et al., "Evaluation of the Effects of Glyceryl Behenate as a Lubricant on the Properties of Directly Compressed Hydrochlorothiazide Tablets", *Pharm. Res.* 5(10): S246 (1988).

Patel et al., "Evaluation of New Lubricants", *Pharm. Res.* 5(10): S247 (1988).

\* cited by examiner

CONTROL RELEASE FORMULATION CONTAINING A HYDROPHOBIC MATERIAL AS THE SUSTAINED RELEASE AGENT

RELATED APPLICATION

The present application is a continuation of application U.S. Ser. No. 10/167,368 filed on Jun. 10, 2002 now U.S. Pat. No. 7,052,706 which is claiming the benefit of Provisional Application U.S. Ser. No. 60/297,140, filed on Jun. 8, 2001.

FIELD OF THE INVENTION

The present invention relates to a controlled release formulation in oral dosage form, preferably in the form of a tablet, containing a hydrophobic material as the sustained release agent.

BACKGROUND OF THE INVENTION

It is of great advantage to both the patient and the physician that medication be formulated so that it may be administered in a minimum number of daily doses from which the drug is uniformly released over a desired extended period of time. This effect is accomplished using sustained or slow release compositions. Sustained or slow release compositions containing pharmaceutical medicaments or other active ingredients are designed to contain higher concentrations of the medicament and are prepared in such a manner as to effect sustained or slow release into the gastrointestinal digestive tract of humans or animals over an extended period of time.

Well absorbed oral sustained or slow release therapeutic drug dosage forms have inherent advantages over conventional, immediate release dosage forms. The advantages include less frequent dosing of a medicament and resultant patient regime compliance, a more sustained drug blood level response, therapeutic action with less ingested drug and the mitigation of side effects. By providing a slow and steady release of the medicament over time, absorbed drug concentration spikes are mitigated or eliminated by effecting a smoother and more sustained blood level response.

For this purpose, a controlled release formulation has to meet some criteria; namely, it must effect an uniform and constant dissolution of the drugs, and it must be effective for an extended period of time. It is also important that such a formulation be simple to make, that the manufacturing process be reproducible and that the product produced by the manufacturing process be uniform. Moreover, if different drugs are used as the active components in the sustained release formulation, it is important that the manufacturing process be easily adaptable to accommodate these various drugs.

Various hydrophilic and hydrophobic materials, including polymers, have been utilized in preparing sustained release formulations. In addition, they have been prepared by various methods, such as solvent evaporation, heat melting, direct compression and wet granulation. Nevertheless, it is well known that the materials used for effecting the controlled release as well as the method of manufacture have a significant effect on the control release performance of the oral dosage form. For example, ethyl cellulose, which is a hydrophobic polymer has been used to effect controlled release of medicaments. However, the release profile is significantly different when it is used as a coating material than when used as a directly compressible powder. Moreover, when matrix type tablets are made with ethyl cellulose using wet granulation methods, the release profile is significantly different from that exhibited by controlled release oral dosage forms prepared by using ethyl cellulose as a directly compressible powder or by using ethyl cellulose as a coating material. Furthermore, if the hydrophobic material is melted in the process of making a sustained release pharmaceutical composition, its release profile is different from that of a controlled release pharmaceutical composition prepared by a different method. These differences in release profile show that the pharmaceutical compositions prepared by the various methods are not the same, but are different.

These differences in release profile are not unique for ethyl cellulose containing pharmaceutical compositions; the release profile of pharmaceutical composition containing other hydrophobic material such as waxes or higher fatty acids or alcohols, and the like, as the controlled release agent are dependent not only upon the identity of the hydrophobic material as controlled release agent, but also upon the method in which the pharmaceutical composition is prepared.

Hydrophobic materials have been used to control the release of medicaments. For example, waxes and lipids have been used as coating material to retard the release of drugs. For instance, the manufacturer of COMPRITOL® 888 (glyceryl behenate), GATTEFOSSE, investigated the effects of coating granules and spheres containing theophylline with COMPRITOL® 888 as a hot melt coating using fluid bed equipment at different concentrations. The wax coating levels of the spherules were 2%, 6% and 10% by weight, respectively. The release profile in water was determined. At 2% levels (w/w) of the wax, 85% of the theophylline was released within one hour. However, at 6% levels of the wax, 55% of the theophylline was released within the first hour, with 35% thereof released in 5 minutes, and at 10% levels (w/w) of the wax, 38% of the theophylline was released within the first hour, with 28% thereof released in 5 minutes. Considering the number of steps used in preparing formulations of this type, this is not an efficient way to formulate controlled released products, and the present inventor sought to find a more efficient process to prepare a controlled release tablet containing a hydrophobic component as the sustained release agent. Moreover, the present inventor also sought to find a method of controlling the release of the drug without placing the wax in a coating, but by blending the hydrophobic material with the drug.

There has been a great deal of literature regarding the use of waxes in controlled release compositions when mixed with medicaments. The common methods of manufacturing sustained release medicaments in oral dosage forms using waxes as the controlled release material admixed with the medicament are (a) melting the drug and wax together, then cooling and milling the melt, and finally tableting after mixing with excipient; (b) using wet granulation techniques, employing an organic solvent as a granulating medium; (c) mixing the drug and waxes in a high shear mixture and using the heat produced during the processing to achieve a homogenous mixture; and (d) using heat radiation to effect melting of the wax in the presence of the drug. All of these methods are cumbersome and can be hazardous.

Most of these techniques use large amounts of waxes to achieve a reasonable controlled release formulation, and the wax is usually present in high concentrations, e.g., greater than 30% (w/w) of the dosage form and in a weight ratio greater than 1:1 relative to the drug. For example, Abdallah in *Alex. J. Pharm.* 1992, 6, 243-246, evaluated three chosen lipophilic polymers, Precirol® ATO 5 (glyceryl palmito stearate), Precirol® wL-2155 (glyceryl stearate) and Compritol® 888 (glycerol behenate) for the preparation of ibuprofen prolonged release compositions. The tablets were prepared by melting the drug and other ingredients with the polymers, cooling the melt and compressing the cooled melt. He found that granules having a size of 200-315 microns prepared with either of the three polymers in a concentration of either 10 or 20% by weight did not exhibit a release retarding effect; the granule formulations prepared with the above-identified lipids in these amounts released the drug completely within 30 minutes. At 50% level of COMPRITOL® 888, however, the granules exhibited a somewhat suitable sustained release profile. However, making a tablet with such a large amount of wax necessarily makes the tablet too large and thus more difficult to swallow, especially for elder patients. The present inventor thus searched for a means of preparing sustained release formulation containing considerably less hydrophobic material.

Perez, et al. in *PRHSJ.* 1993, 12, 263-267 investigated the effect of varying wax levels and methods of matrix formulation on drug release. The amount of drug in the formulation was held at 10% w/w, while the wax level was varied from 10% to 50% w/w. The drug formulations were prepared by two different methods. In one method, designated the physical method, the drug, wax and diluent were blended in a Turbula mixer by geometric dilution for 20 minutes and then the mixture was compressed into a tablet. In the second method, designated the solid dispersion method, the wax was melted and the drug in varying concentrations was incorporated into the melted wax. The molten mixture was allowed to cool until it solidified, and then the solidified mass was granulated through a Stokes oscillating granulator equipped with screen No. 12. Perez, et al. found that tablets prepared by the physical method having the same concentration of wax released the drug at a faster rate than the corresponding drug prepared by the solid dispersion method. Tablets prepared by the physical mixture system containing 30% (w/w) wax released about 79% of drug within about six hours, while in tablets containing 50% (w/w) wax, the drug release was 50% after six hours. On the other hand, tablets prepared by solid dispersion containing 30% (w/w) wax showed a drug release of 72% in six hours, while those tablets prepared by the same method containing 50% (w/w) wax released only 30% of the drug in six hours. Further, they showed that a satisfactory release profile was obtained when the ratio by weight of drug to waxy material was greater than 1:1, e.g., at least 3:1.

Moreover, Perez, et al. showed that at 10% levels of wax (w/w), regardless of which method was used, the release profile was unsatisfactory; the sustained release formulation released about 80% of the drug in about 2 hours when prepared by either method.

The prior art showed that at levels of 30% or higher of the waxy material, acceptable sustained release profiles were obtained, but at lower levels, such as 10%, an unsatisfactory sustained release profile was obtained. Thus, these prior art references teach away from preparing a sustained release formulation containing less than 30% wax.

Reilly, et al. in AAPS 1991 investigated the release profile of acetaminophen at 10% level using glyceryl behenate at various concentrations, 10%, 30% or 50% in spheres and tablets, with the latter being prepared by direct compression or by wet granulation. The reference discloses that simple incorporation of the glyceryl behanate into the spheres did not provide slow release. In the tablets, however, a 10% wax did not provide any sustained release action, but at levels of 30% and 50% by weight (that is, 3:1 or 5:1 weight ratio of glyceryl behanate to drug), the tablets exhibited sustained release action. Moreover, for the tablet formulations, as the amount of wax increased, the amount of sustained release action also increased.

Another investigator Terrier investigated the influence of glycerol palmitostearate on the release of drug. He noted that a tablet containing sodium salicylate as the medicament and glycerol palmitostearate as the excipient in 40% by weight, which was prepared by wet granulation methods, did not exhibit any sustained release. For example, 50% of the drug was released in water after 20 minutes.

The above methods used to prepare the pharmaceutical composition were prepared by methods other than direct compression. However, even if the formulation were prepared by direct compression, the prior art showed that at least 30% of the wax was required in the formulation to effect sustained release. For example, El-Sayed, et al. in *S.T.P. Pharma. Sciences,* 1996, 6, 398-402 prepared a formulation containing 50% theophylline and 30% glyceryl behenate, HPMC or carbopol, and the remainder excipient. Although the tablet so prepared exhibited sustained release formulation, the present inventor searched for a sustained release formulation containing even less than 30% (w/w) wax and a method for preparing same.

The present inventor has found a way to overcome the shortcomings of the prior art and achieve his objective. More specifically, the present invention provides a means of preparing controlled release dosage forms using a simple manufacturing process such as direct compression which involves compression of the various ingredients after a simple mixing procedure. The present inventor has found that effective sustained release formulations can be prepared in this way which incorporates significantly less hydrophobic material than that used heretofore.

SUMMARY OF THE INVENTION

The present invention is directed to a sustained release pharmaceutical composition in tablet form comprising a pharmaceutically effective amount of a medicament and a hydrophobic material as the sustained release agent, said medicament and hydrophobic material being present in the core of the pharmaceutical composition, said core excluding polymer capable of swelling that causes tablet disintegration, including hydrophobic carbohydrate polymer, and excluding high concentrations of low molecular weight water soluble excipients, including lactose, said medicament being present in an amount greater than about 25% (w/w) of the pharmaceutical composition and having a water solubility less than about 1 gram per 10 mL of water at 25° C., said hydrophobic material having a melting point ranging from at least about 40° C. to about 100° C. at 1 atm pressure, and being present in an amount effective to control the release of the medicament, said hydrophobic material being present in an amount ranging from about 3% to about 20% by weight of the pharmaceutical composition and in an amount by weight less than that of the medicament. It is preferred that the pharmaceutical composition is prepared by direct compression without melting the hydrophobic material or the use of a high shear mixer. Although the pharmaceutical composition may be prepared using wet granulation techniques, it is preferred that it is not so prepared.

It is also directed to a method of preparing a sustained release pharmaceutical composition in tablet form which comprises (a) blending a medicament and a hydrophobic material and optionally a lubricant and optionally an excipient and optionally an adjuvant to form a substantially homogenous and uniform blend, said mixture excluding polymer capable of swelling that causes disintegration of the tablet and high concentrations of low molecular weight water soluble excipients, said medicament being present in an amount greater than about 25% by weight of the pharmaceutical composition and having a water solubility less than about 1 gram per 10 mL of water at 25° C., said hydrophobic material having a melting point ranging from at least about 40° C. to about 100° C. at 1 atm pressure, and being present in an amount ranging from about 3% to about 20% by weight of the pharmaceutical composition; and (b) compressing the product of step (a) to form a tablet thereof, said pharmaceutical composition being formed without melting the hydrophobic material or utilizing a high shear mixer. Although the pharmaceutical composition may be prepared by wet granulation, it is not so preferred.

In another embodiment, the present invention is directed to a method of administering to a patient a medicament which comprises (a) preparing a sustained release pharmaceutical composition in tablet form comprising a pharmaceutically effective amount of a medicament and an effective amount of hydrophobic material to control the release of the medicament from the pharmaceutical composition by direct compression without either melting said hydrophobic material or using a high shear mixer, said pharmaceutical composition comprising a core comprising said medicament and said hydrophobic material but excluding any polymer capable of swelling that causes disintegration of the tablet and high concentration of water soluble low molecular weight excipients, said medicament having a water solubility less than about 1 gram per 10 mL of water at 25° C. and being present in the pharmaceutical composition in an amount greater than about 25% by weight and said hydrophobic material having a melting point ranging from about 40° C. to about 100° C. and being present in an amount ranging from about 3% to about 20% by weight of the pharmaceutical composition and in an amount by weight less than that of the medicament and (b) administering the product of step (a) to said patient.

DETAILED DESCRIPTION OF THE PRESENT INVENTION

As described hereinabove, an aspect of the present invention is directed to a sustained release formulation of a pharmaceutically active medicament containing a hydrophobic material having a melting point greater than about 40° C. and less than about 100° C.

As used herein, the terms "drug" and "medicament" and "active substance" are used interchangeably. Moreover, the terms "controlled release" and "sustained release" are used interchangeably. By "sustained release", it is meant, for purposes of the present application, that the therapeutically active medicament or drug is released from the formulation at a controlled rate such that therapeutically beneficial blood levels (below toxic levels) of the medicament in an animal are maintained over an extended period of time, e.g., providing 4, 8, 12, 16 or 24 hours dosage form.

The controlled release formulation of the present invention is to be administered to mammals in need of such treatment wherein the medicament present in the formulation is administered in pharmaceutically effective amounts. By mammals, it is meant a vertebrae of the class mammalia, that is, characterized by possession of hair and mammary glands. Examples include, inter alia, dog, cat, horse, pig, goat, cow, humans and the like. The preferred species of mammal to which the sustained release formulation of the present invention is to be administered is man.

The present pharmaceutical compositions comprises a formulation in unit dosage form. The term "unit dosage form", as employed herein, refers to a physically discrete unit suitable as unitary dosage to mammals, including humans, with each unit containing a predetermined quantity of active material calculated to produce the desired effect in association with the hydrophobic material, the lubricant, if present, the excipient if present or other adjuvants, if present, as described herein.

The present formulation is applicable to a wide variety of drugs or active medicaments suitable for use in sustained release formulation.

Representative medicaments include antacids, anti-inflammatory substances, coronary vasodilators cerebral vasodilators, psychotropics, antimanics, stimulants, anti-histamines, laxatives, decongestants, vitamins, gastrointestinal sedatives, anti-diarrhea preparations, anti-angina drugs, vasodilator anti-arrhythmics, anti-hypertensive drugs, vaconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemia agents, thyroid and anti-thyroid preparations, diuretics, anti-spasmodics, uterine relaxants, mineral and nutritional additives, anti-obesity drugs, anabolic drugs, erythropoietic drugs, anti-asthmatics, expectorants, cough suppressants, mucolytics, anti-uricemic drugs and other drugs or substances acting locally in the mouth, such as topical analgesics, local anesthetics, or combination thereof and the like. The present formulation may contain more than one active ingredient.

The medicament used in the present invention has a low solubility in aqueous solution at 25° C. and 1 atm pressure. It has a water solubility of less than about 1 gram per 10 ml of water at any pH existing in the gastrointestinal tract, typically between a pH of 1 and 7.5. However, if the drug is too insoluble in water then the sustained release formulation prepared therefrom is either too difficult to prepare or does not function effectively as a sustained release pharmaceutical composition. Thus, the drug should have a solubility greater then about 100 mg/liter of water at 25° C.

The drug has preferably a mean particle diameter from about 5 to about 300 microns, more preferably from about 20 to about 200 microns and most preferably from about 30 to about 100 microns.

The preferred medicaments are theophylline, ferrous sulfate, niacin, guaifenesin, clarithromycin, salts of valproic acid, especially Group IA salts thereof e.g., Divalproex sodium, verapamil, dextromethorphan, diclofenac or pharmaceutically acceptable salts thereof, isosorbide mononitrate, levodopa, carbidopa, naproxen, and the like. As one of ordinary skill in the art is well aware, Divalproex is a mixture of about 50% (w/w) sodium or other Group IA metal salt of valproic acid and about 50% (w/w) valproic acid.

The medicament is present in pharmaceutically effective amounts. It is preferred that the medicament is present in amounts ranging from about 25% to about 97% by weight of the pharmaceutical composition.

The pharmaceutical carrier of the present invention is comprised of the hydrophobic material. The hydrophobic material is the sustained release agent. The present pharmaceutical composition does not contain any hydrophilic sustained release agents. The hydrophobic component comprises a water-insoluble wax-like material. The wax-like material comprises a solid generally insoluble substance having a waxy consistency. It should, of course, be ingestible, pharmaceutically acceptable and non-toxic. Many such materials are known and include fats and waxes. Wax, as used herein, is a low melting organic mixture or compound of high molecular weight, and is a solid at room temperature, and is generally similar in composition to fat and oils except that it contains no glycerides. Waxes include higher fatty acids, esters of fatty acid, higher fatty alcohols and mixtures thereof. Fats, on the other hand, are glyceryl esters of higher fatty acids. All of these are hydrophobic materials as the term is used herein.

The hydrophobic material is present in sustained release retarding effective amounts. It is present in the pharmaceutical composition of the present invention in amounts ranging from about 3% to about 20% by weight of the pharmaceutical composition, preferably from about 3% to about 15% by weight more preferably from about 5 to about 15% and most preferably from about 7 to about 12% by weight of the pharmaceutical composition. Thus, it is preferably present in less than 20% by weight.

The hydrophobic material may consist of one component or be a mixture of two or more hydrophobic components, as defined herein.

The hydrophobic material has a melting range above human body temperature, which is about 37° C. The hydrophobic material used in the present invention has a melting point greater than about 40° C., and more preferably greater than about 45° C. However, it is critical that the hydrophobic material have a melting point above human body temperature. Waxes with melting points close to body temperature, such as at 37° C., pose stability problems on storage as well as pose a risk of dose dumping. Thus, the minimum temperature of the hydrophobic material is at about 40° C., i.e., a temperature above which the aforesaid problems do not manifest themselves. It is preferred that the melting point of the hydrophobic material ranges from about 40° C. to about 100° C. and even more preferably from about 45° C. to about 90° C., especially more preferably from about 50° C. to about 80° C. and most preferably from about 55° C. to about 75° C. It is important to note that the presence of lubricants and/or other hydrophobic material may affect the melting range. However, the melting range of the hydrophobic material when associated with these other material in the formulation should not fall below body temperature.

It is preferred that the hydrophobic component has a mean particle size from about 10 microns to about 200 microns. It is more preferred that the mean particle size ranges from about 20 to about 150 microns and most preferably the mean particle size ranges from about 30 to about 100 microns.

As indicated hereinabove, hydrophobic material useful in the present invention includes waxes and neutral fats. As will be described hereinbelow, the hydrophobic material used in the present invention must contain at least 10 carbon atoms.

The useful waxes include those which are obtained from plant and/or animal source or as a petroleum product, i.e., are obtained from natural sources. Examples of this type of preferred waxes include carnauba wax, candelilla wax, spermaceti, beeswax, montan wax, hydrogenated vegetable oil, lecithin, hydrogenated cottonseed oil, hydrogenated tallow, paraffin wax, shellac wax, petrolatum, and the like as well as synthetic waxes, e.g., polyethylene, and the like.

The hydrophobic materials also include fatty acid materials. The fatty acid materials preferably are of the class consisting of fatty acids having 10 to 40 carbons. The fatty acids may be straight chained or branched, but it is preferred that they are straight chained. They may contain no carbon-carbon double bonds, or they may contain carbon-carbon double bonds. If they contain carbon-carbon double bonds, they preferably contain 1, 2, 3 or 4 carbon-carbon double bonds and more preferably 1 or 2 carbon-carbon double bonds. Examples include stearic acid, palmitic acid, lauric acid, eleostearic acids, a mixture of stearic acid and palmitic acid, e.g., 85 wt % stearic acid and 15 wt % palmitic acid, and the like.

The fatty acid materials also include fatty alcohols having from 16 to 44 carbon atoms. They also may be straight chain or branched, but it is preferred that they are straight chained. They may be completely saturated or contain carbon-carbon double bonds. If they contain carbon-carbon double bonds, they preferably contain 1, 2, 3 or 4 carbon-carbon double bonds and more preferably 1 or 2 carbon-carbon double bonds. Examples include stearyl alcohol, cetyl alcohol, palmitol and the like.

The fatty acid material also includes a fatty amine having 13 to 45 carbons and a fatty amide having 11 to 45 carbons.

The hydrophobic material also includes neutral lipids. The neutral lipids are preferably of the class consisting of monoglycerides, diglycerides, triglycerides.

The monoglycerides, diglycerides and triglycerides are of the formula:

$$\begin{array}{l} CH_2-OR_1 \\ CH-OR_2 \\ CH-OR_3 \end{array}$$

wherein $R_1$ is hydrogen or

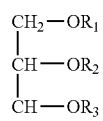

$R_2$ is hydrogen or

$R_3$ is hydrogen or

and $R_4$, $R_5$ and $R_6$ are independently alkyl or alkenyl, said alkyl and alkenyl groups having from 9 to 39 carbon atoms and wherein at least one of $R_1$, $R_2$ and $R_3$ is other than hydrogen.

The alkyl groups and alkenyl groups of $R_4$, $R_5$ and $R_6$ may be branched and are preferably straight chained. The alkenyl groups may contain 1, 2, 3 or 4 carbon-carbon double bonds and if present, they more preferably contain 1 or 2 carbon-carbon double bonds.

Examples include glyceryl behenate, glyceryl palmitostearate, glyceryl monostearate, polyglycolyzed glycerides and the like.

Besides glycerol esters, the hydrophobic material includes other fatty acid esters of polyhydric alcohols having two or more hydroxy groups in the molecules which may be esterified to one or more fatty acids, as defined herein, having the aforesaid characteristics described hereinabove, such as the melting point in the range indicated hereinabove. Examples of said polyhydric alcohols include alkylene glycols, such as ethylene glycol and propylene glycol. It is preferred that the polyhydric alcohols contain two or three hydroxy groups. The polyhydroxy alcohol is esterified to at least one fatty acid, as defined herein. The preferred fatty acids have the formula $R_4COOH$, wherein $R_4$ in each fatty acid may be the same or different and is as defined hereinabove.

The hydrophobic material also includes pharmaceutically acceptable salts of fatty acids, as long as the fatty acid has a melting point in the range indicated hereinabove. The fatty acid is as defined hereinabove. Examples include magnesium stearate and calcium and aluminum salts of palmitic acid, and the like.

It is preferred that the hydrophobic material is a fatty acid, or salt thereof, fatty alcohol, a wax or a neutral lipid. It is more preferred that the hydrophobic material is a mono, di or triglyceride which is esterified to a fatty acid.

The most preferred hydrophobic materials are glyceryl behenate, glyceryl palmitostearate, glyceryl monostearate, polyglycolized glycerides, stearic acid, hydrogenated vegetable oil, cetyl alcohol or mixtures thereof. The most preferred hydrophobic material is glyceryl behenate.

The present pharmaceutical composition excludes in the core of the tablet in which the medicament and the sustained release agent described hereinabove are present, any ingredient that can cause disintegration of the tablet. This includes any polymer, such as hydrophilic polymers capable of swelling or hydrophobic carbohydrate polymers, as described hereinbelow. Moreover, since high concentrations of low molecular weight water soluble excipients can cause disintegration of the tablet, they are also excluded in the core. As used herein, the term "high concentration of low molecular weight water soluble excipients" refers to low molecular weight water soluble excipents being present in concentrations greater than or equal to about 20% (w/w) of the tablet. In other words, the core of the pharmaceutical compositions of the present invention may include low molecular weight excipients as long as their concentration is less than about 20% by weight of the tablet. It is more preferred that the concentration thereof is less than about 10% by weight of the tablet (w/w).

The low molecular weight water soluble excipients are well known to one of ordinary skill in the art. As defined herein, a "low molecular weight water soluble excipient" refers to a water soluble excipient having a molecular weight of less than about 1000 daltons. Examples of low molecular weight water soluble excipients include lactose, sucrose, glucose, citric acid, sodium phosphate, buffering agents and the like. Thus, if the low molecular weight excipient has a solubility in water greater than about 1 gm in 20 ml of water at 25° C. and 1 atmosphere pressure and more preferably greater than about 1 gram in 10 ml of water at 25° C. and 1 atmosphere pressure it is not present in the core of the tablet at high concentrations, as defined hereinabove. The water soluble low molecular weight excipient is present in less than about 20% by weight of the tablet and more preferably less than about 10% by weight of the tablet. By low molecular weight excipient, it is meant that an excipient has a molecular weight of less than 1000 daltons.

Thus, the present compositions preferably do not contain any polymer capable of swelling or any low molecular weight excipients such as lactose in high concentration. Thus, the hydrophobic material excludes hydrophobic carbohydrate polymers, especially since they do not melt in the aforesaid ranges. As defined herein hydrophobic carbohydrate polymers are hydrophobic cellulose derivatives in which the R moiety of the cellulose-R or cellulose-ROH or other R derivatives are either an aliphatic acyl group of 2 to 100 carbons or larger or aliphatic alkyl containing from 1 to 100 carbons or larger or chitin. Examples of hydrophobic polymers which are excluded from the hydrophobic material used herein are ethyl cellulose, propyl cellulose, cellulose acetate, cellulose propionate, cellulose acetate-butyrate, cellulose acetate propionate, and the like. Moreover, the hydrophobic material excludes the hydrated alkyl cellulose e.g., hydroxy alkyl cellulose.

Since the sustained release retarding agent of the pharmaceutical composition of the present invention is a hydrophobic material, and excludes polymers that swell, it excludes hydrophilic compounds as the sustained release agent, including hydrocolloids, as well as any gel forming substances, e.g., xanthan gum, guar gum, hydroxypropylmethycellulose, methacrylate or acrylate polymers and the like. In addition, it excludes proteins.

Without wishing to be bound, it is believed that the controlled release of the medicament is achieved because of the presence of a non-disintegrating dosage which is rendered partially insoluble because of the wax. The wax helps control the release. By being insoluble in water, the wax makes the pharmaceutical composition containing same at least partially insoluble if not fully insoluble in water. If the excipient is insoluble also, together the wax and the excipient strengthen the tablet. The rate of dissolution or diffusion is controlled both by controlled erosion as well as controlled solubility.

On the other hand, any ingredient which can disrupt the tablet surfaces, such as polymers which can swell or disintegrating agents will weaken the matrix (core) and cause the tablet to disintegrate. In fact, it is believed that the reason that in the prior art, high concentrations of wax were used is because it contained swelling or disintegrating agents.

Other causes of disintegration includes high levels of soluble ingredients, including low molecular weight water soluble excipients discussed hereinabove.

However, polymers whether it be insoluble or soluble which do not swell are not excluded by the present invention. Moreover, water soluble excipients which have molecular weights greater than 1000 daltons are also not excluded and may be present in the tablet of the present pharmaceutical composition, including the core thereof in concentrations greater than or less than 20% (w/w) by weight of the tablet. Thus, for example, maltodextrin is water soluble and is a polymer, but it does not cause disintegration because it does not swell. It may be present in the tablet, including the core at concentrations greater than or less than 20% by weight. Also polyethylene glycols with molecular weights greater than 1000 daltons may be present in the pharmaceutical compositions, including the core of the tablet in concentrations greater than or than about 20% by weight of the tablet. These are completely water soluble, but they can be used because they do not swell and the and the high molecular weight PEG's retard disintegration.

Moreover, water insoluble excipients, may be present in concentrations greater than or less than about 20% of the tablet. These include microcrystalline cellulose, dicalcium phosphate and the like.

In the pharmaceutical composition of the present invention, the sustained release agent is the hydrophobic material. It is admixed with the active medicament; it is present in the central core with the pharmaceutical composition. If the pharmaceutical composition contains a coating, the coating does not contain the sustained release agent.

Moreover, if the coating is present, it may contain swellable polymers, or disintegrating agents, including low molecular weight water soluble excipients, since these are outside (on the surface) of the tablet. Thus, the polymers capable of swelling although cannot be present in the core of the tablet may be present in the coating of the pharmaceutical composition of the present invention. Moreover, the restriction on the concentrations of the water soluble excipients refers to their presence in the core of the pharmaceutical compositions. There is no restriction thereon if the water soluble excipients are present in the coating. However, it is preferred that the tablet does not contain a coating. But, if a coating is present, the water soluble low molecular weight excipients and the swellable polymers are each preferably present in less than about 20% of the pharmaceutical composition and more preferably in less than about 10% of the pharmaceutical composition. Further, if a coating is present, it is preferred that it does not contain disintegrating agents and it is also preferred that it does not contain water swelling polymers.

Without wishing to be bound, it is believed that the hydrophobic material interacts with the medicament and retards it from being released from the oral dosage form. More specifically, the hydrophobic substances used in the present invention are believed to form water insoluble matrices which remain intact for an elongated period of time, allowing leaching or diffusion of the drug at a controlled rate.

The inventor has found that the amount by weight of the hydrophobic material used is less than that of the medicament. Thus, the weight ratio of hydrophobic material to medicament is less than 1:1 by weight. It is preferred that the weight ratio of medicament to hydrophobic material ranges from about 9:1 to about 5:4. Without wishing to be bound, it is believed that the smaller amount of hydrophobic material makes the dosage form more stable and physically stronger. The concentration of hydrophobic material used is reasonably small, allowing formation of very hard tablets, which can withstand various rigors. It is also believed, without wishing to be bound, that the use of hydrophobic material having melting point ranges higher than human body temperature also contributes to the stability of the dosage form and predictability of the in vivo release of the medicament. Without wishing to be bound, it is believed that the heat generated during compression may cause softening of the wax, helping it to form a continuous matrix and particle coating of the formulation ingredients. The dosage form produced by the process described hereinabove is believed, without wishing to be bound, to release the drug by erosion and diffusion from an essentially non-disintegrating matrix.

The present formulation also contains optional components. For example, although not necessary, in a preferred embodiment, the present formulation additionally contains a lubricant that is typically used in the pharmaceutical arts in oral tablets. As used herein, the term "lubricant" refers to a material which can reduce the friction between the die walls and the punch faces which occurs during the compression and ejection of a tablet. The lubricant prevents sticking of the tablet material to the punch faces and the die walls. As used herein, the term "lubricant" includes anti-adherents. Examples of lubricants include stearate salts, e.g., alkali, alkaline earth, and transition metal salts thereof, e.g., calcium, magnesium, or zinc; stearic acid, polyethylene oxide, talc, hydrogenated vegetable oil, and vegetable oil derivatives, fumed silica, silicones, high molecular weight polyalkylene glycol, e.g., high molecular weight polyethylene glycol, monoesters of propylene glycol, saturated fatty acids containing about 8-22 carbon atoms and preferably 16-20 carbon atoms. The preferred lubricants are the stearate salts, stearic acid, talc and the like.

When a lubricant is used, it is present in a lubricating effective amount of the lubricant. Preferably, the lubricant is present in amounts ranging from about 0.1% to about 5% by weight and more preferably from about 1% to about 3% by weight of the tablet.

Another optional ingredient is an inert filler (excipient). The filler may be substantially water-soluble or water insoluble. A filler is used if needed or desired although not necessary for the present formulation. The fillers used in the present formulation are those typically used in the pharmaceutical arts for oral dosage forms, such as tablets. Examples include calcium salts, such as calcium sulfate, dicalcium phosphate, tricalcium phosphate, calcium lactate, calcium gluconate, and the like, glycerol phosphate; citrates; and mixture thereof, and the like. However, the inert filler of the sustained release formulation of the present invention may contain a pharmaceutically acceptable saccharide, including a monosaccharide, a disaccharide, or a polyhydric alcohol and/or mixtures of any of the foregoing. Examples thereof include sucrose, dextrose, polydextrose, maltodextrin, microcrystalline cellulose, fructose, xylitol, sorbitol, mixtures thereof and the like. The preferred excipient is maltodextrin.

Thus, another embodiment of the present invention comprises a pharmaceutically effective amount of a medicament and a hydrophobic material as the sustained released agent and maltodextrin, in the absence of lactose and hydrophobic carbohydrate polymers, said medicament being present is an amount greater than about 25% (w/w) of the pharmaceutical composition and having a water solubility less than about 1 gram for 10 ml of water at 25° C. and 1 atm pressure and greater than about 100 mg/liter of water at 25° C. and 1 atm pressure, said hydrophobic material having a melting point ranging from at least about 40° C. to about 100° C. at 1 atm pressure and being present in an amount effective to control the release of the medicament, said hydrophobic material being present in an amount ranging from about 3% to about 20% by weight of the pharmaceutical composition and in an amount by weight less than that of said medicament.

It is also preferred that the pharmaceutical composition does not contain lactose. Lactose is undesirable for several reasons. First, many people suffering from lactose intolerance will have difficulty in digesting an oral dosage form containing same. In addition, lactose interacts with various drugs containing certain functional group e.g., amines, thereon. Although it may be used, it is preferred that the pharmaceutical composition of the present invention does not contain a disaccharide.

The filler, if present, is present in amounts ranging from but about 0% (but greater than 0) to about 72% by weight.

Other optional ingredients (adjuvants) that are also typically used in pharmaceuticals may also be present, such as coloring agents, preservatives (e.g., methylparabens), artificial sweeteners, flavorants, anti-oxidizing agents and the like. Artificial sweeteners include, but are not limited to saccharin sodium, aspartame, dipotassium glycyrrhizinate, stevia, thaumatin and the like. Flavorants include, but are not limited to lemon, lime, orange and menthol. The colorants include, but are not limited to various food colors, e.g., FD & C colors, such as FD & C Yellow No. 6, food lakes and the like. Examples of anti-oxidants include ascorbic acid, sodium metabisulphite, and the like. These optional ingredients, if present, are preferably present in amounts ranging from about 0.1% to about 5% by weight of the tablet and most preferably less than about 3% (w/w) of the tablet.

However, it is preferred that the component in the greatest concentration is the medicament. Moreover, it is preferred that the sum of medicament and hydrophobic material is greater than 45% by weight of the oral dosage form, and more preferably greater than about 60% by weight of the pharmaceutical composition.

The present formulation of the present invention is prepared by blending the medicament with the hydrophobic material and lubricant, if present, the filler, if present, and the adjuvants, if present. The ingredients are mixed in a typical blender that is normally utilized in the pharmaceutical arts, such as a Hobart mixer, V-blender, a planetary mixer, Twin shell blender and the like. The ingredients are blended together typically at about ambient temperature; no additional heating is necessary, although slight modifications of temperature therefrom could be utilized. It is preferred that the blending be conducted at temperatures ranging from about 10° C. to about 35° C. The hydrophobic material is not melted. Moreover, if the components are heated, the elevated temperature used in the present process is not even substantially close to the melting point of the hydrophobic material. The pharmaceutical composition of the present invention is not prepared by thermal infusion.

The ingredients in the formulation are preferably mixed together in a large batch using techniques well known in the pharmaceutical arts and are intimately intermixed until the mixture is homogenous with respect to the drug. The term "homogenous" with respect to the drug is used to denote that the various components are substantially uniform throughout the invention, i.e., a substantially homogeneous blend is formed.

When the mixture is homogeneous the unit dosage form is prepared by techniques known in the art. Thus, the mixture may be made into a pellet, capsule, granule, pill, tablet or other unit dosage form using conventional techniques known in the art.

The preferred unit oral dosage form is a tablet. The tablet can be prepared by the following procedure.

A unit dosage amount of the homogenous mixture is compressed into a tablet form using a tablet machine typically utilized in the pharmaceutical arts. More specifically, the mixture is fed to the die of a tablet press and sufficient pressure is applied to form a solid tablet. Such pressure can vary, and typically ranges from about 1,000 psi to about 6,000 psi and preferably about 2,000 psi force. The solid formulation according to the present invention is compressed to a sufficient hardness to prevent the premature ingress of the aqueous medium into the tablet. Preferably, the formulation is compressed into a tablet form which is of the order of 5-20 Kp and more preferably 8-20 Kp as determined by a Schleuniger hardness tested.

In a variation, all of the above steps are repeated, except that the mixing is initially performed in the absence of a lubricant, if a lubricant is to be added to the formulation. When the mixture is homogeneous with respect to the drug, then the lubricant is added and the mixing is continued until the lubricant, if present, may be substantially evenly dispersed in the mixture. Then the mixing is terminated, and the mixture is immediately thereafter made into a unit dosage form. For example, it may be compressed into a tablet, as described hereinabove.

Prior to the mixing step, the individual components may optionally be milled, e.g., passed through a screen, sieve, etc. to reduce the size of the particles thereof. Alternatively, the substantially uniformly blended mixture prior to the formation of the unit dosage form. For example, if it is a tablet, the mixture may be milled before the compression step.

In the process described herein, unlike most methods, the hydrophobic material is not melted, either separately from the other components of the pharmaceutical composition or with other components of the pharmaceutical composition. More specifically, in the process of the present invention, the components in the mixing step are not heated to temperatures at or substantially close to the melting temperature of the hydrophobic material. The present invention avoids the disadvantages associated with heat melting. First, heat labile compounds will decompose in the molten hydrophobic material, e.g., wax. Further, it is expensive and hazardous to adopt this molten wax technique to mass production. Aside from the hazards of working with large quantities of molten material, there is the difficulty of working with the hard congealed-medicament mixture which must be removed from the mixing vessel and sized. Additionally, the sizing of the hard congealed-medicament mixture exposes the previously encased medicament, thereby detracting from its controlled release profile in subsequence dosage forms. A further outstanding disadvantage of the known art method of preparing sustained release tablets, in particular, by the molten heat process is that a high dosage drug cannot be easily prepared with satisfactory release characteristics. The present inventor has found that he is able to prepare a pharmaceutical composition having excellent sustained release properties without melting the hydrophobic component, e.g., wax.

In addition, the present inventor has found that he is able to obtain a substantially homogenous blend without subjecting the components to high shear mixing. Moreover, as indicated hereinabove, the methodology described hereinabove is simple and economical and avoids the expense associated with the high shear mixer. Moreover, the present inventor has found that the present method provides a pharmaceutical composition with excellent sustained release properties.

Moreover, the methodology used in the present invention to prepare the pharmaceutical composition does not utilize wet granulation. Thus, the present process does not have the disadvantages associated with wet granulation. It avoids the hazards associated with the use of toxic or flammable solvents used in wet granulation methods.

This method used in the present process for preparing the sustained release pharmaceutical composition of the present invention has several advantages. It is a simple and efficient method of manufacturing, more so than if the composition were prepared by melting the hydrophobic material or utilizing a high shear mixer. It overcomes the drawbacks of formulating with hydrophobic material, e.g., waxes, such as dimensional stability, with respect to heat and abrasion. The hydrophobic material is not melted or heated to just below melting temperatures such as by utilizing such techniques as radiation heating. In a preferred embodiment, the hydrophobic material is mixed with the other components at temperatures no higher than slightly elevated over room temperature, but substantially less than the melting temperatures of the hydrophobic material. This technique minimizes the heat and energy in the manufacture of unit dosage forms of the present invention relative to that used in the prior art, thereby making the present process more efficient. In a preferred embodiment, no granulating solvents are required, thus in this embodiment, the present methods avoid the risks of toxicity and fires that are potentially present when using the wet granulation methods in preparing sustained release pharmaceuticals.

After the unit dosage form, e.g., tablet, is formed, it may be coated with materials normally used in pharmaceuticals, if desired. If coated, the coating is prepared by techniques known in the art, but the hydrophobic material used as the controlled release agent is not present in the coating. However, the formulation of the present invention is preferably uncoated.

The unit dosage form prepared by the present invention has the properties typically found in the pharmaceutical art. For example, if the unit dosage form is a tablet, the tablet product is obtained which has the desired hardness and friability typically found for pharmaceutical tablets. The hardness is preferably 5-25 Kp and more preferably 8-20 Kp.

The present formulation in unit dosage form, e.g., tablet form, has an excellent drug release profile. The release profile of the pharmaceutical formulation of the present invention is non-linear. For example, it has a predetermined controlled and sustained action and a regular delayed pattern so that the medicament is available over a period of up to 36 hours, depending upon the type of unit dosage form used, the precise size of the unit dosage form, the identity of the active ingredient, aqueous solubility of the active ingredient, hardness and the particular carrier composition. For example, in accordance with the process of the present invention, a controlled release pharmaceutical composition can be prepared wherein the release time is 2-4 hours, 8 to 10 hours, 15-18 hours, 20-24 hours, etc. as desired. Furthermore, the release profile of each formulation is substantially uniform. Finally, if the oral dosage form is a tablet, the tablets prepared in accordance with the present invention are hard and dense, have low friability and provide controlled and sustained release over an extended period. Solid dry forms prepared by the present invention are stable and their release rate does not change to any significant (if any) extent over an extended period of storage.

The sustained release medicament is provided in solid form, conveniently in a unit dosage form. It is preferred to provide the sustained release medicament in solid unit dosage form for oral administration, especially in tablet form. Preferably, it is intended to release the pharmacologically active ingredient slowly or according to a prescribed rate after ingestion within the body as the formulation progresses along the gastro-intestinal tract. In this regard, the gastro-intestinal tract is considered to be the abdominal portion of the alimentary canal, i.e., the lower end of the esophagus, the stomach and the intestines.

The dosages of a formulation administered to a mammal in need thereof according to the invention, correspond to the normal dosages of the particular active ingredient known to the skilled artisan. The precise amount of drug administered to a patient will depend on a number of factors, including the age of the patient, the severity of the condition and the past medical history, among other factors, and always lie within the sound discretion of the administering physician. For guideline as a suitable dosage, reference is made to the Physicians Desk Reference.

The pharmaceutical composition formed is preferably not multi-layered, but is only one layer.

Unless indicated to the contrary, all percentages are weight percentages relative to the oral dosage form. Moreover, unless indicated to the contrary, the active ingredient, the hydrophobic material, and any other optional ingredients, e.g., lubricant, excipient, and other ingredients are calculated on a dry weight basis, without reference to any water or other component present.

Moreover, as used herein, the singular shall refer to the plural and vice versa.

The following non-limiting examples further illustrate the present invention.

EXAMPLE 1

Ferrous sulfate (160 mg), glyceryl behenate (30 mg) and maltodextrin (110 mg) were thoroughly mixed together in a V blender for one hour and compressed into a tablet using a rotary tablet press. The dissolution was determined using USP apparatus I in water. The release profile is as follows:

| Time (in hours) | % Drug Release (w/w) |
|---|---|
| 1 | 36 |
| 2 | 58 |
| 3 | 72 |
| 4 | 82 |

EXAMPLES 2-6

The following ingredients were mixed in a suitable blender for 1 hour.

| Component | EX. 2 | EX. 3 | EX. 4 | EX. 5 | EX. 6 |
|---|---|---|---|---|---|
| Theophylline | 600 mg | 600 mg | 600 mg | 400 mg | 400 mg |
| Glyceryl behenate | 60 mg | 60 mg | 60 mg | 40 mg | 50 mg |
| Maltodextrin | — | 29.5 mg | 36.5 mg | 23 mg | 13 mg |
| Fumed Silica | — | 3.5 mg | 3.5 mg | 2.4 mg | 2.4 mg |
| Magnesium stearate | — | 7 mg | — | 4.7 mg | 4.7 mg |

The resulting mixture was compressed into a tablet using a rotary tablet press. The dissolution of each formulation was determined using USP apparatus I in water. The release profile is as follows:

| Time in Hours | % Released (w/w) | | | | |
|---|---|---|---|---|---|
| | EX. 2 | EX. 3 | EX. 4 | EX. 5 | EX. 6 |
| 1 | 13 | 16 | 12 | 17 | 14 |
| 3 | 24 | 25 | 22 | 29 | 26 |
| 5 | 32 | 36 | 30 | 38 | 33 |
| 7 | 38 | 42 | 34 | 45 | 39 |
| 9 | — | 47 | 37 | — | — |
| 12 | — | 54 | 44 | — | — |

EXAMPLE 7

Clarithromycin (500 mg), glyceryl behenate (25 mg), silicified microcrystalline cellulose (220.15 mg), and maltodextrin (220.15 mg) were passed twice through a 40 mesh screen. The various ingredients were mixed in a double cone blender for 30 minutes. Magnesium stearate (14.7 mg) was added to the mixture which was stirred for another fifteen minutes. The mixture was compressed into a tablet. The tablets were punched using a 20×10 mm capsule shaped punch. The tablet contained 500 mg clarithromycin and 980 mg total weight.

The dissolution was determined using USP apparatus I in acetate buffer, pH 5.0. The release profile was as follows:

| Time (in hours) | % Release (w/w) in acetate buffer pH 5.0 |
|---|---|
| 1 | 10.92 |
| 3 | 28.31 |
| 5 | 49.81 |
| 7 | 72.04 |
| 9 | 87.95 |
| 12 | 92.45 |

EXAMPLE 8

A tablet of divalproex sodium was prepared as follows:

Divalproex sodium (576.21 mg), glyceryl behenate (190 mg), polyvinyl pyrrolidone (47.5 mg), dibasic calcium phosphate dihydrate (44.4 mg), silicified microcrystalline cellulose (44.4 mg) and aerosol (19 mg) were passed twice through a 40 mesh screen. The various ingredients were mixed in a double cone blender for 30 minutes. Magnesium stearate (28.5 mg) was added to the mixture and the mixture was stirred for another fifteen minutes. The mixture was compressed into a tablet. The tablets were punched using a 20×10 mm capsule shaped punch. The tablet contained 576.21 mg of diralproex sodium and 950 mg total weight.

The dissolution was determined using U.S.P apparatus I in water. The release profile was as follows.

| Time (in hours) | % Release in water (w/w) |
|---|---|
| 1 | 25.87 |
| 3 | 39.30 |
| 5 | 47.46 |
| 7 | 55.02 |

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the appended claims.

What is claimed is:

1. A sustained release pharmaceutical composition in unit dosage form comprising a core comprising one or more medicaments selected from the group consisting of guaifenesin, clarithromycin, dextromethorphan, theophylline, divalproex sodium, diclofenac sodium, niacin, ferrous sulfate, verapamil, levodopa, isosorbide mononitrate, carbidopa, and naproxen and a hydrophobic material as a sustained release agent, and optionally a lubricant, and optionally an excipient and optionally an adjuvant, the one or more medicaments being present in said composition in an amount greater than about 25% by weight of the pharmaceutical composition said hydrophobic material containing 10 or more carbon atoms and having a melting point ranging from at least about 40° C. to about 100° C., and being present in an amount ranging from about 3% to less than about 20% by weight of the pharmaceutical composition and in an amount by weight less than that of the one or more medicaments, and wherein said composition excludes any ingredient in the core that causes the disintegration of the unit dosage form, said pharmaceutical composition being prepared by blending said medicament and hydrophobic material and optionally said lubricant and optionally said excipient and optionally said adjuvant at a temperature below that of the melting point of the hydrophobic material to form a substantially homogenous and uniform blend, and forming therefrom the sustained release pharmaceutical composition in unit dosage form, said pharmaceutical composition being formed in the absence of thermal infusion or melting the hydrophobic material or utilizing a high shear mixer or by heating to temperatures slightly below the melting point of the hydrophobic material.

2. The pharmaceutical composition according to claim 1 wherein the unit dosage form is uncoated.

3. The pharmaceutical composition according to claim 1 wherein the hydrophobic material is present in an amount ranging from about 5% to about 15% by weight of the pharmaceutical composition.

4. The pharmaceutical composition according to claim 3 wherein the hydrophobic material is present in an amount ranging from about 7% to about 12% by weight of the pharmaceutical composition.

5. The pharmaceutical composition according to claim 1 wherein the weight ratio of the one or more medicaments to hydrophobic material ranges from about 9 to 1 to about 5:4.

6. The pharmaceutical composition according to claim 1 wherein the melting point of the hydrophobic material ranges from about 40° C. to about 90° C.

7. The pharmaceutical composition according to claim 6 wherein the melting point of the hydrophobic material ranges from about 50° C. to about 80° C.

8. The pharmaceutical composition according to claim 7 wherein the melting point of the hydrophobic material ranges from about 55° C. to about 75° C.

9. The pharmaceutical composition according to claim 1 wherein the hydrophobic material has a mean particle size ranging from about 10 microns to about 200 microns.

10. The pharmaceutical composition according to claim 9 wherein the hydrophobic material has a mean particle size ranging from about 30 to about 100 microns.

11. The pharmaceutical composition according to claim 1 wherein the medicament is present in an amount ranging from about 25% to about 97% by weight of the pharmaceutical composition.

12. The pharmaceutical composition according to claim 11 wherein the medicament is present in an amount ranging from about 35% to about 90% by weight of the pharmaceutical composition.

13. The pharmaceutical composition according to claim 12 wherein the medicament is present in an amount ranging from about 40% to about 85% by weight of the pharmaceutical composition.

14. The pharmaceutical composition according to claim 1 wherein a lubricant is additionally present.

15. The pharmaceutical composition according to claim 14 wherein an excipient is additionally present.

16. The pharmaceutical composition according to claim 1 wherein an excipient is additionally present.

17. The pharmaceutical composition according to claim 15 where the excipient is maltodextrin.

18. The pharmaceutical composition according to claim 16 wherein the excipient is maltodextrin.

19. The pharmaceutical composition according to claim 1 wherein the hydrophobic material is a fatty acid or salt thereof or a monoglyceride, diglyceride or triglyceride.

20. The pharmaceutical composition according to claim 1 wherein the hydrophobic material is glyceryl behenate, hydrogenated vegetable oil, stearic acid, glyceryl monostearate, glycerylpalmito stearate or cetyl alcohol.

21. The pharmaceutical composition according to claim 1 wherein the hydrophobic material is a fatty acid having 10 to 30 carbons or salt thereof, a fatty alcohol having from 10 to 44 carbon atoms, or

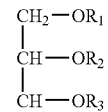

wherein $R_1$ is hydrogen or

$R_2$ is hydrogen or

$R_3$ is hydrogen or

wherein $R_4$, $R_5$ and $R_6$ are independently lower alkyl or lower alkenyl having from 9 to 29 carbon atoms and wherein at least one of $R_1$, $R_2$ and $R_3$ is other than hydrogen.

22. The pharmaceutical composition according to claim 1 wherein an excipient is present and is insoluble in water.

23. The pharmaceutical composition according to claim 1 wherein a water soluble excipient is present, said water soluble excipient being present in less than about 20% (w/w) by weight of the pharmaceutical composition.

24. The pharmaceutical composition according to claim 1 in the form of a tablet.

25. A sustained release pharmaceutical composition in unit dosage form comprising a core comprising one or more medicaments selected from the group consisting of theophylline, guaifenesin, clarithromycin, and niacin, and a hydrophobic material as a sustained release agent, and optionally a lubricant, and optionally an excipient and optionally an adjuvant, the one or more medicaments being present in said composition in an amount greater than about 25% by weight of the pharmaceutical composition said hydrophobic material containing 10 or more carbon atoms and having a melting point ranging from at least about 40° C. to about 100° C. at 1 atm pressure, and being present in an amount ranging from about 3% to less than about 20% by weight of the pharmaceutical composition and in an amount by weight less than that of the one or more medicaments, and wherein said composition excludes any ingredient in the core that causes the disintegration of the unit dosage form, said pharmaceutical composition being prepared by blending said medicament and hydrophobic material and optionally said lubricant and optionally said excipient and optionally said adjuvant at a temperature below that of the melting point of the hydrophobic material to form a substantially homogenous and uniform blend, and forming therefrom the sustained release pharmaceutical composition in unit dosage form, said pharmaceutical composition being formed in the absence of thermal infusion or melting the hydrophobic material or utilizing a high shear mixer or by heating to temperatures slightly below the melting point of the hydrophobic material.

26. The pharmaceutical composition according to claim 25 wherein the hydrophobic material is glyceryl behenate.

* * * * *